United States Patent
Platt, Jr.

(10) Patent No.: US 8,251,995 B2
(45) Date of Patent: Aug. 28, 2012

(54) ARTICULATING IONIZABLE GAS COAGULATOR

(75) Inventor: Robert C. Platt, Jr., Laguna Niguel, CA (US)

(73) Assignee: Covidien AG (CH)

( * ) Notice: Subject to any disclaimer, the term of this patent is extended or adjusted under 35 U.S.C. 154(b) by 421 days.

(21) Appl. No.: 12/535,799

(22) Filed: Aug. 5, 2009

(65) Prior Publication Data
US 2010/0016856 A1    Jan. 21, 2010

Related U.S. Application Data

(63) Continuation of application No. 11/099,039, filed on Apr. 5, 2005, now Pat. No. 7,578,818, which is a continuation of application No. 10/282,288, filed on Oct. 28, 2002, now Pat. No. 6,911,029, which is a continuation of application No. 09/665,380, filed on Sep. 21, 2000, now Pat. No. 6,475,217.

(60) Provisional application No. 60/157,743, filed on Oct. 5, 1999.

(51) Int. Cl.
*A61B 18/18* (2006.01)
(52) U.S. Cl. .......................................... 606/49; 606/41
(58) Field of Classification Search .................. 606/40, 606/41, 49, 50
See application file for complete search history.

(56) References Cited

U.S. PATENT DOCUMENTS

| | | |
|---|---|---|
| 330,253 A | 11/1885 | Melhorn |
| 2,708,933 A | 5/1955 | August |
| 2,828,747 A | 4/1958 | August |
| 3,434,476 A | 3/1969 | Shaw et al. |
| 3,569,661 A | 3/1971 | Ebeling |
| 3,595,239 A | 7/1971 | Petersen |
| 3,692,973 A | 9/1972 | Oku et al. |
| 3,699,967 A | 10/1972 | Anderson |
| 3,832,513 A | 8/1974 | Klasson |
| 3,838,242 A | 9/1974 | Goucher |
| 3,903,891 A | 9/1975 | Brayshaw |
| 3,970,088 A | 7/1976 | Morrison |
| 3,987,795 A | 10/1976 | Morrison |
| 3,991,764 A | 11/1976 | Incropera et al. |
| 4,014,343 A | 3/1977 | Esty |
| 4,019,925 A | 4/1977 | Nenno et al. |
| 4,040,426 A | 8/1977 | Morrison, Jr. |
| 4,041,952 A | 8/1977 | Morrison, Jr. et al. |
| 4,043,342 A | 8/1977 | Morrison, Jr. |
| 4,057,064 A | 11/1977 | Morrison, Jr. et al. |

(Continued)

FOREIGN PATENT DOCUMENTS

DE    3710489    11/1987

(Continued)

OTHER PUBLICATIONS

U.S. Appl. No. 08/383,162, filed Feb. 3, 1995.

(Continued)

*Primary Examiner* — Roy Gibson

(57) ABSTRACT

A method for coagulating tissue is disclosed. The method includes the steps of providing an electrosurgical apparatus including: an elongated flexible tube having a proximal end and a distal end and defining a longitudinal axis and at least one electrode mounted proximate to the tube for ionizing pressurized ionizable gas. The method also includes the steps of moving the distal end of the tube from a first position wherein the distal end is disposed in a generally parallel fashion relative to the tissue to a second position wherein the distal end directs pressurized ionizable gas flowing through the tube at an angle α with respect to the longitudinal axis and igniting the pressurized ionized gas through the at least one electrode.

8 Claims, 5 Drawing Sheets

U.S. PATENT DOCUMENTS

| | | |
|---|---|---|
| 4,060,088 A | 11/1977 | Morrison, Jr. et al. |
| 4,209,018 A | 6/1980 | Meinke et al. |
| 4,242,562 A | 12/1980 | Karinsky et al. |
| 4,311,145 A | 1/1982 | Esty et al. |
| 4,492,231 A | 1/1985 | Auth |
| 4,492,845 A | 1/1985 | Kljuchko et al. |
| 4,545,375 A | 10/1985 | Cline |
| 4,577,637 A | 3/1986 | Mueller, Jr. |
| 4,601,701 A | 7/1986 | Mueller, Jr. |
| 4,665,906 A | 5/1987 | Jervis |
| 4,708,137 A | 11/1987 | Tsukagoshi |
| 4,711,238 A | 12/1987 | Cunningham |
| 4,728,322 A | 3/1988 | Walker et al. |
| 4,732,556 A | 3/1988 | Chiang et al. |
| 4,753,223 A | 6/1988 | Bremer |
| 4,781,175 A | 11/1988 | McGreevy et al. |
| 4,817,613 A | 4/1989 | Jaraczewski et al. |
| 4,822,557 A | 4/1989 | Suzuki et al. |
| 4,864,824 A | 9/1989 | Gabriel et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,931,047 A | 6/1990 | Broadwin et al. |
| 4,955,863 A | 9/1990 | Walker et al. |
| 5,015,227 A | 5/1991 | Broadwin et al. |
| 5,041,110 A | 8/1991 | Fleenor |
| 5,061,268 A | 10/1991 | Fleenor |
| 5,061,768 A | 10/1991 | Kishimoto et al. |
| 5,067,957 A | 11/1991 | Jervis |
| 5,088,997 A | 2/1992 | Delahuerga et al. |
| 5,098,430 A | 3/1992 | Fleenor |
| 5,108,389 A | 4/1992 | Cosmescu |
| RE33,925 E | 5/1992 | Bales et al. |
| 5,122,138 A | 6/1992 | Manwaring |
| D330,253 S | 10/1992 | Burek |
| 5,152,762 A | 10/1992 | McElhenney |
| 5,160,334 A | 11/1992 | Billings et al. |
| 5,163,935 A | 11/1992 | Black et al. |
| 5,195,959 A | 3/1993 | Smith |
| 5,195,968 A | 3/1993 | Lundquist et al. |
| 5,207,675 A | 5/1993 | Canady |
| 5,217,457 A | 6/1993 | Delahuerga et al. |
| 5,234,457 A | 8/1993 | Andersen |
| 5,242,438 A | 9/1993 | Saadatmanesh et al. |
| 5,244,462 A | 9/1993 | Delahuerga et al. |
| 5,248,311 A | 9/1993 | Black et al. |
| 5,256,138 A | 10/1993 | Burek et al. |
| RE34,432 E | 11/1993 | Bertrand |
| 5,292,320 A | 3/1994 | Brown et al. |
| 5,306,238 A | 4/1994 | Fleenor |
| 5,324,283 A | 6/1994 | Heckele |
| 5,330,469 A | 7/1994 | Fleenor |
| RE34,780 E | 11/1994 | Trenconsky et al. |
| 5,366,456 A | 11/1994 | Rink et al. |
| 5,370,649 A | 12/1994 | Gardetto et al. |
| 5,380,317 A | 1/1995 | Everett et al. |
| 5,389,390 A | 2/1995 | Kross |
| 5,476,461 A | 12/1995 | Cho et al. |
| 5,496,308 A | 3/1996 | Brown et al. |
| 5,537,499 A | 7/1996 | Brekke |
| 5,554,172 A | 9/1996 | Heim |
| 5,620,439 A | 4/1997 | Abela et al. |
| 5,653,689 A | 8/1997 | Buelna et al. |
| 5,662,621 A | 9/1997 | Lafontaine |
| 5,669,904 A | 9/1997 | Platt, Jr. et al. |
| 5,669,907 A | 9/1997 | Platt, Jr. et al. |
| 5,688,261 A | 11/1997 | Amirkhanian et al. |
| 5,700,260 A | 12/1997 | Cho et al. |
| 5,707,402 A | 1/1998 | Heim |
| 5,716,365 A | 2/1998 | Goicoechea et al. |
| 5,720,745 A | 2/1998 | Farin et al. |
| 5,782,860 A | 7/1998 | Epstein et al. |
| 5,782,896 A | 7/1998 | Chen et al. |
| 5,797,920 A | 8/1998 | Kim |
| 5,800,500 A | 9/1998 | Spelman et al. |
| 5,800,516 A | 9/1998 | Fine et al. |
| 5,821,664 A | 10/1998 | Shahinpoor |
| 5,836,944 A | 11/1998 | Cosmescu |
| 5,848,986 A | 12/1998 | Lundquist et al. |
| 5,855,475 A | 1/1999 | Fujio et al. |
| 5,908,402 A | 6/1999 | Blythe |
| 5,964,714 A | 10/1999 | Lafontaine |
| 5,972,416 A | 10/1999 | Reimels et al. |
| 6,039,736 A | 3/2000 | Platt |
| 6,080,183 A | 6/2000 | Tsugita et al. |
| 6,102,940 A | 8/2000 | Robichon et al. |
| 6,117,167 A | 9/2000 | Goicoechea et al. |
| 6,139,519 A | 10/2000 | Blythe |
| 6,149,648 A | 11/2000 | Cosmescu |
| 6,197,026 B1 | 3/2001 | Farin et al. |
| 6,213,999 B1 | 4/2001 | Platt, Jr. et al. |
| 6,264,650 B1 | 7/2001 | Hovda et al. |
| 6,348,051 B1 | 2/2002 | Farein et al. |
| 6,458,125 B1 | 10/2002 | Cosmescu |
| 6,475,217 B1 | 11/2002 | Platt |
| 6,558,383 B2 | 5/2003 | Cunningham et al. |
| 6,592,583 B2 | 7/2003 | Hirano et al. |
| 6,602,249 B1 | 8/2003 | Stoddard |
| 6,616,660 B1 | 9/2003 | Platt |
| 6,638,274 B2 | 10/2003 | Yamamoto |
| 6,666,865 B2 | 12/2003 | Platt |
| 6,740,081 B2 | 5/2004 | Hilal |
| 6,852,112 B2 | 2/2005 | Platt |
| 6,911,029 B2 | 6/2005 | Platt |
| 7,033,353 B2 | 4/2006 | Stoddard |
| 7,044,950 B2 | 5/2006 | Yamamoto |
| 7,175,336 B2 | 2/2007 | Voellmicke et al. |
| 7,311,708 B2 | 12/2007 | McClurken |
| 7,549,990 B2 | 6/2009 | Canady |
| 7,572,255 B2 | 8/2009 | Sartor et al. |
| 7,578,817 B2 | 8/2009 | Canady |
| 7,578,818 B2 | 8/2009 | Platt |
| 7,601,150 B2 | 10/2009 | Farin |
| 7,608,839 B2 | 10/2009 | Coulombe et al. |
| 7,628,787 B2 | 12/2009 | Sartor et al. |
| 2005/0015086 A1 | 1/2005 | Platt |
| 2006/0052771 A1 | 3/2006 | Sartor |
| 2006/0052774 A1 | 3/2006 | Garrison et al. |
| 2006/0088581 A1 | 4/2006 | Blaszczykiewicz et al. |
| 2006/0200122 A1 | 9/2006 | Sartor et al. |
| 2007/0208337 A1 | 9/2007 | Podhajsky et al. |
| 2007/0213709 A1 | 9/2007 | Podhajsky |
| 2008/0215045 A1 | 9/2008 | Platt |
| 2009/0048594 A1 | 2/2009 | Sartor et al. |
| 2009/0054893 A1 | 2/2009 | Sartor et al. |
| 2009/0054896 A1 | 2/2009 | Fridman et al. |
| 2009/0076505 A1 | 3/2009 | Arts |
| 2009/0216226 A1 | 8/2009 | Davison et al. |
| 2009/0275941 A1 | 11/2009 | Sartor et al. |

FOREIGN PATENT DOCUMENTS

| | | |
|---|---|---|
| DE | 4139029 | 6/1993 |
| DE | 4326037 | 2/1995 |
| DE | 9117019 | 4/1995 |
| DE | 19537897 | 3/1997 |
| DE | 9117299 | 4/2000 |
| DE | 19848784 | 5/2000 |
| DE | 29724247 | 8/2000 |
| DE | 19524645 | 11/2002 |
| EP | 0447121 | 9/1991 |
| EP | 0612535 | 8/1994 |
| EP | 0956827 | 11/1999 |
| EP | 1090599 | 4/2001 |
| EP | 1127551 | 8/2001 |
| EP | 1199037 | 4/2002 |
| EP | 1199038 | 7/2003 |
| EP | 1323384 | 7/2003 |
| EP | 1561430 | 8/2005 |
| EP | 1570798 | 9/2005 |
| EP | 1595507 | 11/2005 |
| FR | 1340509 | 9/1963 |
| GB | L1014995 | 12/1965 |
| JP | 61-159953 | 7/1986 |
| SU | 1438745 | 11/1988 |
| WO | WO 91/13593 | 9/1991 |
| WO | WO 93/03678 | 3/1993 |
| WO | WO 96/24301 | 8/1996 |

| WO | WO 96/27337 | 9/1996 |
| WO | WO 99/15091 | 4/1999 |
| WO | WO 01/62333 | 8/2001 |
| WO | WO 02/058762 | 8/2002 |
| WO | WO 2004/026150 | 4/2004 |
| WO | WO 2005/016142 | 2/2005 |
| WO | WO 2009/0146432 | 12/2009 |
| WO | WO 2009/0146439 | 12/2009 |

OTHER PUBLICATIONS

U.S. Appl. No. 08/619,380, filed Mar. 21, 1996.
U.S. Appl. No. 08/621,151, filed Mar. 21, 1996.
U.S. Appl. No. 08/878,694, filed Jun. 19, 1997.
U.S. Appl. No. 09/270,856, filed Mar. 17, 1999.
U.S. Appl. No. 09/504,640, filed Feb. 16, 2000.
U.S. Appl. No. 09/666,312, filed Sep. 21, 2000.
U.S. Appl. No. 12/191,799, filed Aug. 14, 2008.
U.S. Appl. No. 12/535,799, filed Aug. 5, 2009.
U.S. Appl. No. 12/606,672, filed Sep. 30, 2009.
U.S. Appl. No. 12/622,248, filed Nov. 19, 2009.
Grund et al., "Endoscopic Argon Plasma . . . Flexible Endoscopy"; Endoscopic Surgery and Allied Technologies, No. 1, vol. 2, pp. 42-46 (Feb. 1994).
Farin et al., Technology of Argon Plasma . . . Endoscopic Applications; Endoscopic Surgery and Allied Technologies, No. 1, vol. 2, pp. 71-77 (Feb. 1994).
Brand et al., "Electrosurgical Debulking of Ovarian Cancer: A New Technique Using the Argon Beam Coagulator"; Gynecologic Oncology 39 pp. 115-118 (1990).
Hernandez et al., "A Controlled Study of the Argon Beam Coagultor for Partial Nephrectomy"; The Journal of Urology, vol. 143, May (J. Urol. 143: pp. 1062-1065, 1990).
Ward et al., "A Significant New Contribution to Radical Head and Neck Surgery"; Arch Otolaryngology, Head and Neck Surg., vol. 115 pp. 921-923 (Aug. 1989).
Mark H. Mellow, "The Role of Endoscopic Laser Therapy in Gastrointestinal Neoplasms"; Advanced Therapeutic Endoscopy, pp. 17-21, 1990.
Silverstein et al., "Thermal Coagulation Therapy for Upper Gatrointestinal Bleeding"; Advanced Therapeutic Endoscopy, pp. 79-84, 1990.
Waye et al., "Endoscopic Treatment Options"; Techniques in Therapeutic Endoscopy, pp. 1.7-1.15, 1987.
European Search Report EP 01 10 2843.8-2305, dated May 15, 2001.
European Search Report EP 05 00 2257, dated Jun. 1, 2005.
European Search Report EP 06 01 9572 dated Nov. 21, 2006.
European Search Report EP 07 00 4356 dated Jul. 2, 2007.
European Search Report EP 07 00 4659 dated Feb. 19, 2008.
European Search Report EP 07 00 4659—partial dated May 24, 2007.
International Search Report PCT/US98/19284, dated Jan. 14, 1999.

ARTICULATING IONIZABLE GAS COAGULATOR

CROSS-REFERENCE TO RELATED APPLICATION

The present application is a continuation of U.S. patent application Ser. No. 11/099,039 filed on Apr. 5, 2005 by Robert C. Platt, now U.S. Pat. No. 7,578,818, which is a continuation U.S. patent application Ser. No. 10/282,288 filed on Oct. 28, 2002 now U.S. Pat. No. 6,911,029 by Robert C. Platt, which is a continuation of U.S. patent application Ser. No. 09/665,380 filed on Sep. 21, 2000 now U.S. Pat. No. 6,475,217 by Robert C. Platt, which claims priority to U.S. Provisional Application Ser. No. 60/157,743 filed on Oct. 5, 1999, the entire contents of all of which are hereby incorporated by reference herein.

TECHNICAL FIELD

The present disclosure relates to gas-enhanced electrosurgical instruments for coagulating tissue. More particularly, the present disclosure relates to an articulating, gas-enhanced electrosurgical apparatus for coagulating tissue.

BACKGROUND OF RELATED ART

Over the last several decades, more and more surgeons are abandoning traditional open methods of gaining access to vital organs and body cavities in favor of endoscopes and endoscopic instruments which access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, and this presents a design challenge to instrument manufacturers who must find ways to make surgical instruments that fit through the cannulas and operate in a safe and effective manner.

Endoscopic instruments for arresting blood loss and coagulating tissue are well known in the art. For example, several prior art instruments employ thermal coagulation (heated probes) to arrest bleeding. However, due to space limitations surgeons can have difficulty manipulating the instrument to coagulate, desiccate, fulgurate and/or cut tissue. Moreover, if the probe comes into close contact with the tissue, the probe may adhere to the eschar during probe removal possibly causing repeat bleeding. Other instruments direct high frequency electric current through the tissue to stop the bleeding. Again, eschar adherence may also be a problem with these instruments. In both types of instruments, the depth of the coagulation is difficult to control.

U.S. Pat. No. 5,207,675 to Canady attempts to resolve certain of the above-noted problems with respect to the prior art by providing a tube-like coagulation instrument in which an ionizable gas is forced through the instrument and ionized by an electrode in the region between the distal end of the instrument and the bleeding tissue. The electrode, then, does not contact the tissue.

U.S. Pat. No. 5,720,745 to Farin et al. discloses a coagulation instrument which extends through a working channel of an endoscope and includes an electrode for ionizing a stream of ionizable gas exiting the distal end of the instrument at a rate of less than about 1 liter/minute. As explained in detail in the Farin et al. specification, the purpose of discharging the gas at a very low flow rate is to effectively cloud the tissue area and create an ionizable gas "atmosphere" to gently coagulate the tissue.

Using these instruments to treat certain more tubular sites, e.g., the esophagus and/or colon, is often difficult, impractical and time consuming. For example, these longitudinally oriented instruments fire the ionized gas and the RF energy in an axial direction from their respective distal ends which, in the case of tubular tissue, would be parallel to the bleeding tissue. Thus, manipulating these instruments to focus the energy transversely or off-axis at the bleeding tissue may be very difficult.

Thus, a need exists for the development of a new and effective instrument for treating certain more tubular tissue.

SUMMARY

The present disclosure relates to an electrosurgical apparatus for coagulating tissue which includes an elongated flexible tube having a proximal end, a distal end a source for supplying pressurized ionizable gas to the proximal end of the tube. The apparatus in one embodiment includes a hollow sleeve made from a shape memory alloy, e.g., Nitinol and/or Tinel, which has a generally curved austenite state and displays stress-induced martensite behavior at normal body temperatures. The hollow sleeve is restrained in a deformed stress-induced martensite configuration within the tube wherein partial extension of a portion of the hollow sleeve from the tube transforms the portion from the deformed configuration to its generally curved austenite configuration such that the portion directs the gas transversely at the tissue. The surgical apparatus also includes at least one active electrode and a source of high frequency electrical energy for ionizing the gas prior to the gas exiting the portion of the sleeve.

Preferably, the angle at which the gas is directed at the tissue is directly related to the distance the portion of the sleeve extends from the tube.

In another embodiment of the present disclosure, the electrosurgical apparatus includes a wire connected to the distal end of the tube. The wire is movable from a first generally relaxed position wherein the tube is disposed in generally rectilinear parallel fashion relative to the tissue to a second retracted position wherein the distal end of the tube flexes at an angle to direct the gas towards the tissue. Preferably, the angle at which the gas is directed at the tissue is directly related to the amount of tension placed on the wire.

Another embodiment includes a corona electrode disposed proximate the distal end of the tube for inducing ignition of the plasma prior to emission. A wire is used to articulate the distal end of the tube and direct the gas at the tissue. Preferably, the wire is connected to the corona electrode and electrically connects the corona electrode to a source of electrosurgical energy. A dielectric material is preferably disposed between the corona electrode and the active electrode to prevent arcing between electrodes.

BRIEF DESCRIPTION OF THE DRAWINGS

Various embodiments of the subject instrument are described herein with reference to the drawings wherein.

DETAILED DESCRIPTION OF THE PREFERRED EMBODIMENTS

Figure 1:
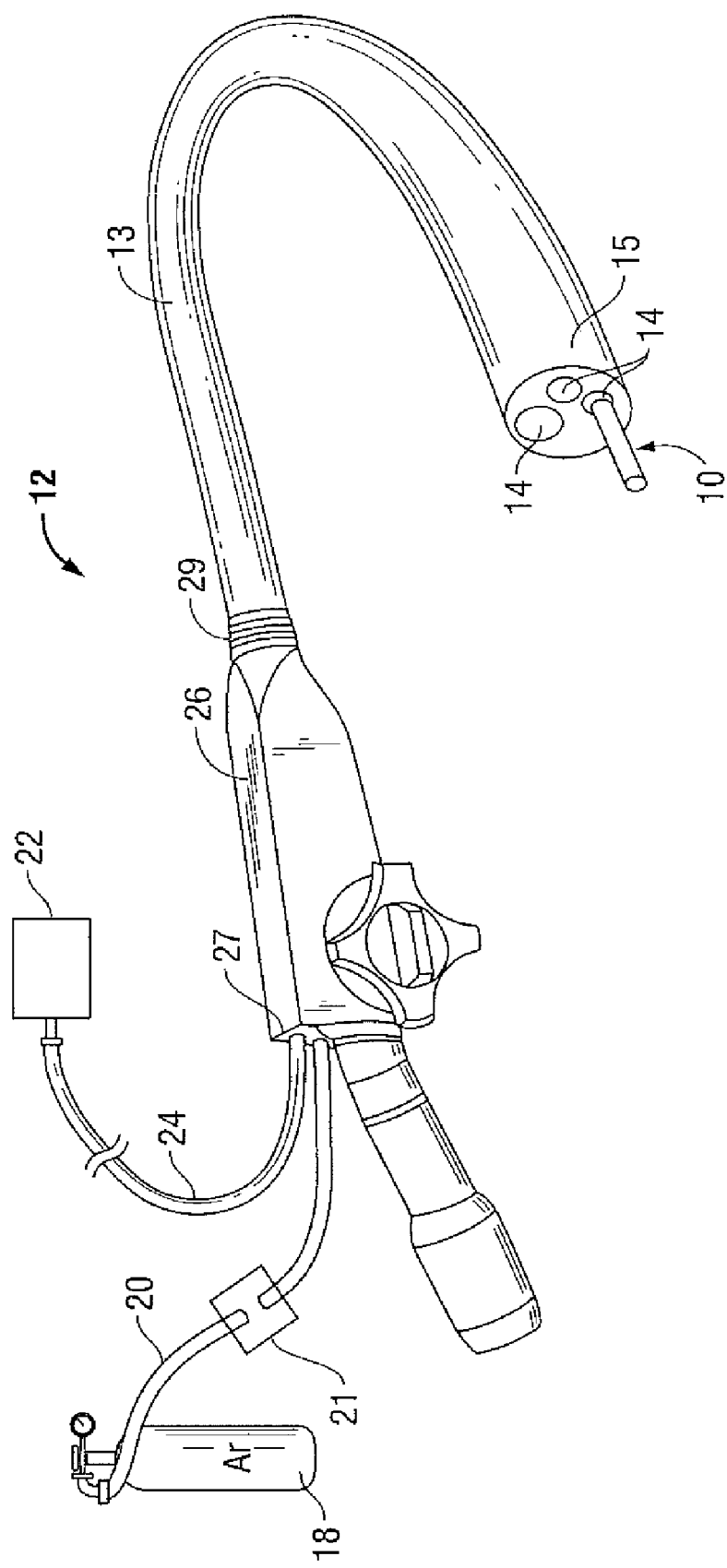
FIG. 1 is a front, perspective view of an electrosurgical instrument shown extending through a working channel of a flexible endoscope.

Referring now to FIG. 1, an articulating tissue coagulator generally identified by reference numeral 10 is shown extending through a working channel of an endoscope 12. Preferably, the coagulator 10 can be employed with a variety of different endoscopes such as those manufactured by Olympus, Pentax and Fujinon. As such, only the basic operating features of the endoscope 12 which work in combination with the present disclosure need to be described herein. For example, endoscope 12 includes a handpiece 26 having a proximal end 27 and a distal end 29. In the drawings and in the description which follows, the term "proximal", as is traditional, will refer to the end of the apparatus which is closer to the user, while the term "distal" will refer to the end which is further from the user.

Preferably, the proximal end of the coagulator 10 is mechanically coupled to a supply 18 of pressurized ionizable gas, e.g., inert gas, by way of hose 20 and electrically coupled to an electrosurgical generator 22 by way of cable 24 to supply a source of electrosurgical energy, e.g., high frequency coagulation current. It is envisioned that the electrosurgical generator 22 selectively controls the amount of electrosurgical energy transmitted to an electrode during a surgical procedure. It is also envisioned that the supply of pressurized ionizable gas selectively controls the rate of flow of gas. A pressure regulator, designated by reference numeral 21, is preferably provided to regulate the fluid pressure.

As shown in FIG. 1, a long, flexible tubular member 13 having one or more of working channels 14 located therein is mechanically coupled to the distal end 29 of the handpiece 26. Preferably, at least one of the working channels 14 is sufficiently dimensioned to receive the coagulator 10 of the present disclosure. Other working channels 14 can be utilized to receive other surgical instruments and accessories such as graspers and biopsy forceps.

Turning now to FIGS. 1, 2A, 2B and 3, one preferred embodiment of the coagulator 10 is shown therein and includes an elongated, generally flexible catheter or tube 30 having a proximal end 32 which extends through a working channel 14 of the endoscope 12 and a distal end 34 which projects outwardly from the distal end 15 of tube 13. Ionizable gas 28, e.g., argon, is supplied to the proximal end 32 of the coagulator 10 by a gas conduit (not shown) located inside tube 13. Preferably, gas 28 is supplied from source 18 to the coagulator 10 at a selectable, predetermined flow rate and flows generally within the tube 30 in the direction of the arrow towards the distal end 34 of tube 30. Advantageously, the flow rate of the gas 28 is selectively adjustable and can easily be regulated depending upon a particular purpose or a particular surgical condition.

Electrode 48 produces an RF electric field, which ionizes the gas 28 in the region between the electrode and the tissue 50. Electrode 48 is connected by way of an electrical conduit (not shown) disposed within tubes 30 and 13 which is ultimately connected to electrosurgical generator 22. Preferably, the electrode 48 is ring or pin-type and is spaced from the distal end 34 such that the electrode 48 cannot come into contact with the tissue 50 during the surgical procedure. A return electrode or pad 17 is positioned on the patient and is electrically coupled to the electrosurgical generator 22 to provide a return path for the electrosurgical current.

Preferably, a stream of gas plasma 46 conducts the current to the tissue 50 while effectively scattering blood away from the treatment site allowing the tissue 50 to readily coagulate and arrest bleeding. A gas plasma 46 is an ionized gas that is used in surgical procedures to conduct electrosurgical energy to a patient without electrode contact by providing a pathway of low electrical resistance. The electrosurgical energy will follow this path and can therefore be used to coagulate, desiccate, or fulgurate blood or tissue 50 of the patient. One of the advantages of this procedure is that no physical contact is required between an electrode 48 and the tissue 50 being treated. One advantage of having a directed flow of gas 28 is that the plasma arc can be accurately focused and directed by the flow.

Figure 2A:
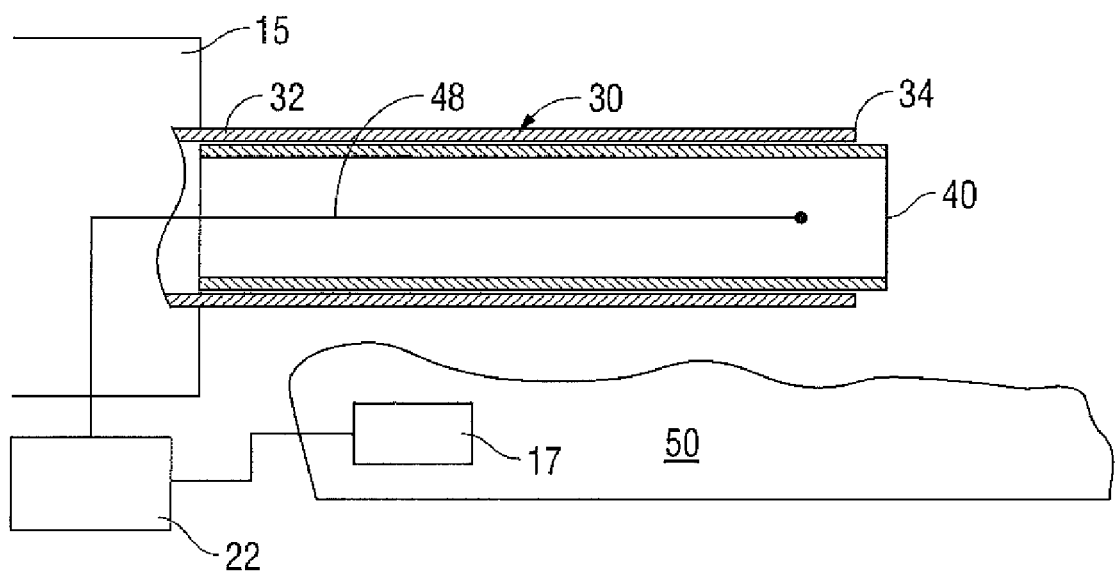
FIG. 2A is an enlarged, side sectional view of one embodiment of the present disclosure showing a hollow shape memory sleeve in retracted position within a catheter.
Figure 2B:
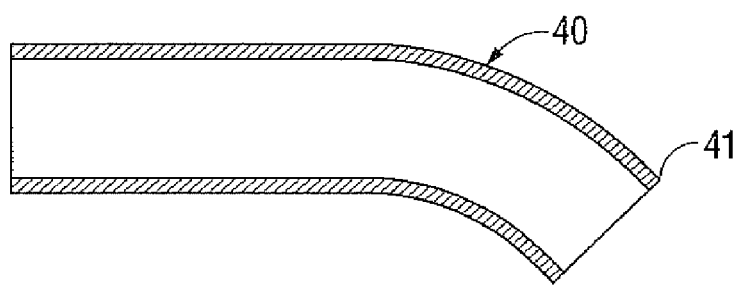
FIG. 2B is an enlarged view of the hollow shape memory sleeve shown in austenite configuration.
Figure 3:
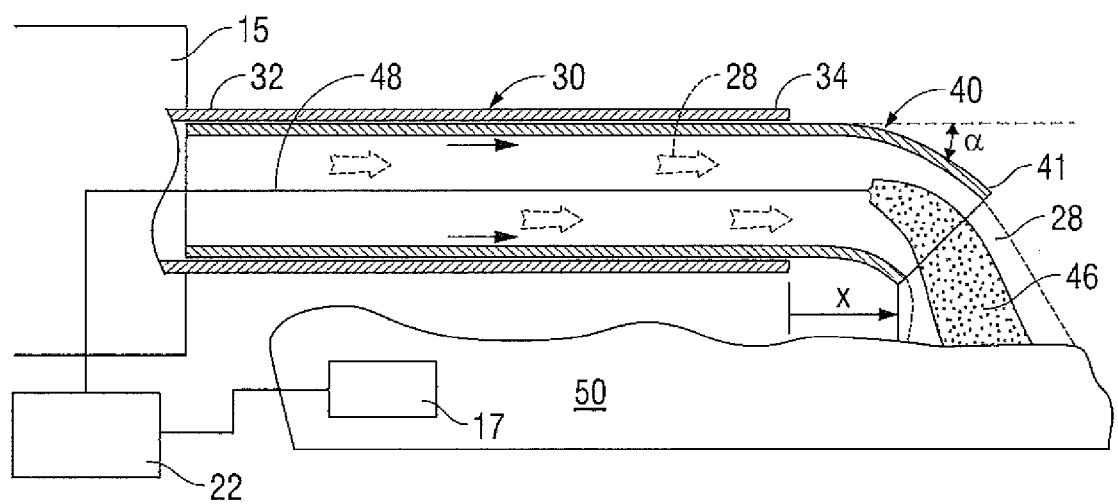
FIG. 3 is an enlarged, side sectional view of the shape memory sleeve of FIGS. 2A and 2B shown extending and articulating from the catheter to direct ionized gas at the tissue.

As best seen in FIGS. 2A, 2B and 3, one approach for manipulating and/or directing the plasma/ionized gas 46 emitting from the distal end 34 of the tube 30 is to implant a hollow sleeve 40 having shape memory characteristics within the distal end 34 of the tube 30. Preferably, as the sleeve 40 is extended from the distal end 34 of the tube 30, the sleeve 40 flexes and directs the ionized gas 46 towards the tissue 50.

More particularly, shape memory alloys (SMAs) are a family of alloys having anthropomorphic qualities of memory and trainability and are particularly well suited for use with medical instruments. SMAs have been applied to such items as actuators for control systems, steerable catheters and clamps. One of the most common SMAs is Nitinol which can retain shape memories for two different physical configurations and changes shape as a function of temperature. Recently, other SMAs have been developed based on copper, zinc and aluminum and have similar shape memory retaining features.

SMAs undergo a crystalline phase transition upon applied temperature and/or stress variations. A particularly useful attribute of SMAs is that after it is deformed by temperature/stress, it can completely recover its original shape on being returned to the original temperature. The ability of an alloy to possess shape memory is a result of the fact that the alloy undergoes a reversible transformation from an austenite state to a martensite state with a change in temperature (or stress-induced condition). This transformation is referred to as a thermoplastic martensite transformation.

Under normal conditions, the thermoelastic martensite transformation occurs over a temperature range which varies with the composition of the alloy, itself, and the type of thermal-mechanical processing by which it was manufactured. In other words, the temperature at which a shape is "memorized" by an SMA is a function of the temperature at which the martensite and austenite crystals form in that particular alloy. For example, Nitinol alloys can be fabricated so that the shape memory effect will occur over a wide range of temperatures, e.g., −270° to +100° Celsius.

Many SMAs are also known to display stress-induced martensite (SIM) which occurs when the alloy is deformed from its original austenite state to a martensite state by subjecting the alloy to a stress condition. For example and with respect to FIGS. 2A, 2B and 3 of the present disclosure, hollow sleeve 40 is generally bent or L-shaped when disposed in its original or austenite state (see FIG. 2B). When sleeve 40 is inserted into the tube 30, sleeve 40 is deformed, i.e., straightened, into a stress-induced martensite state enabling the user to more easily insert through the endoscope navigate the tube 30 through tight body cavities and passageways to access damaged tissue 50.

As seen best in FIG. 3, after insertion of the tube 30 into the body cavity/passageway, the user can easily direct the ionized gas 46 flowing through the tube 30 transversely (off-axis) at the tissue 50 by extending the sleeve 40 distally which causes the extended portion of the sleeve 40 to revert back to its original/austenite state (it is assumed that the temperature of use of the alloy allows spontaneous reversion when stress is removed). The user can also control the angle $s_x$ of the ionized gas 46 being directed at the tissue 50 by controlling the distance "X" that the sleeve 40 extends from the tube 30. Preferably, angle α and distance "X" are directly related, i.e., as distance "X" increases angle α increases.

It is envisioned that by empowering the user to articulate, i.e., bend, the distal end 41 of the sleeve 40 at various angle α will enable the operator to more effectively coagulate bleeding tissue 50 with more longitudinal-type lesions, i.e., tissue lesions which run parallel to the axial direction of endoscope 12, and without causing collateral tissue damage. It is also envisioned that by adjusting the angle α of the distal end 41 of the sleeve 40, the angle with respect to the tissue surface or longitudinal axis of the tube at which the ionized gas 46 impinges can be selectively controlled.

Figure 4:
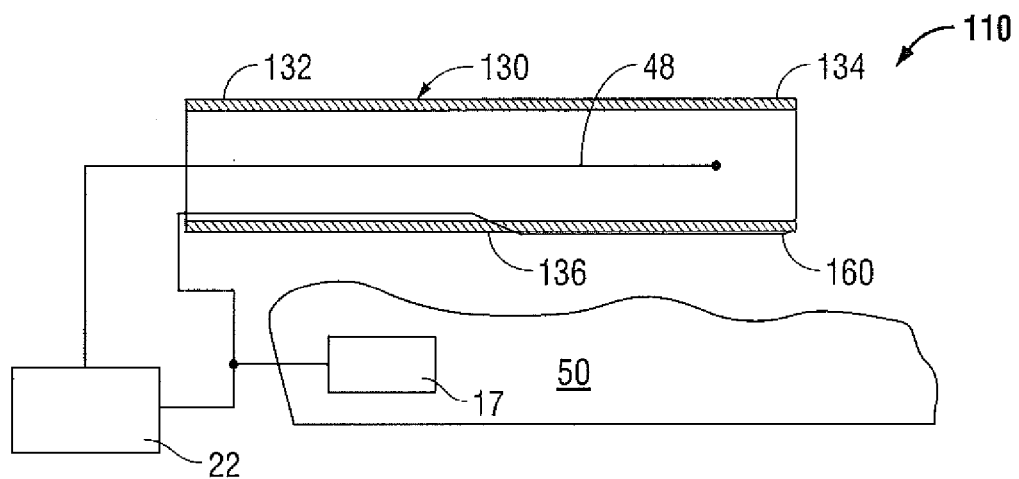
FIG. 4 is an enlarged, side sectional view of another embodiment of the present disclosure showing a pull wire/return electrode affixed at the distal end of a flexible catheter.
Figure 5:
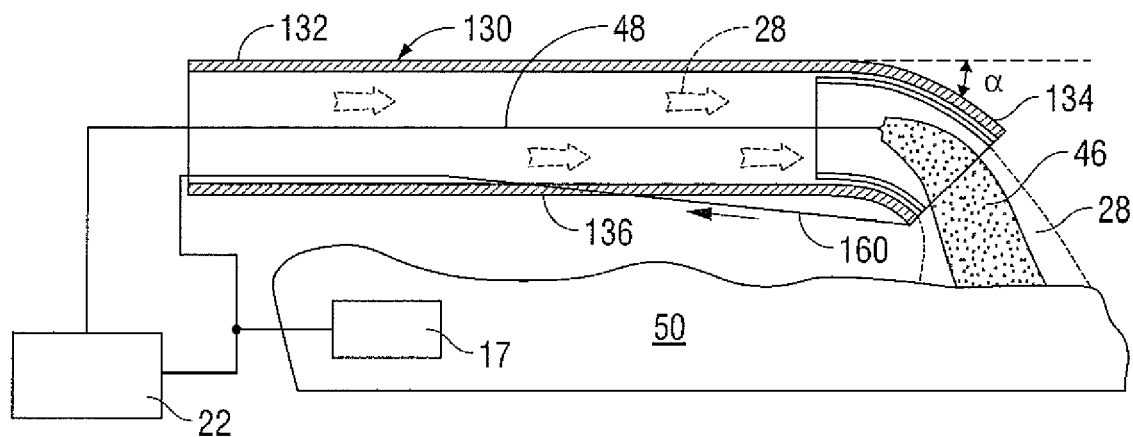
FIG. 5 is an enlarged, side sectional view of the embodiment of FIG. 4 showing the wire being drawn to articulate the flexible catheter and direct ionized gas at the tissue.

FIGS. 4 and 5 show another embodiment of an articulating coagulator 110 which includes an elongated tube 130 having a proximal end 132 and a distal end 134. Preferably, tube 130 is flexible at or proximate the distal end 134 of tube 130. Ionizable gas 28 is supplied to the proximal end 132 of the coagulator 110 at a selectable predetermined flow rate and flows generally within the tube 130 in the direction of the arrow towards the distal end 134 of tube 130. Advantageously, the flow rate of the gas 28 is selectively adjustable and can easily be regulated depending upon a particular purpose or a particular surgical condition. Much in the same manner as described with respect to FIGS. 2A, 2B and 3, electrode 48 discharges an electrosurgical current which ionizes gas 28 prior to gas 28 emission.

Coagulator 110 also includes a pull wire 160 which is connected at one end proximate the distal end 134 of tube 130 such that retraction of wire 160 flexes tube 130. Preferably, wire 160 is disposed within the proximal end 132 of tube 130 and exits a port 136 disposed within tube 130 to attach to tube 130 at a point proximate distal end 134. Wire 160 is movable from a first generally relaxed position wherein tube 30 is disposed in a generally rectilinear fashion relative to tissue 50 (see FIG. 4) to a second retracted or tensed position wherein the distal end 134 of tube 130 flexes towards tissue 50 (see FIG. 5). The user can easily direct the ionized gas 46 flowing through the tube 130 transversely at tissue 50 by controlling the tensile force applied to wire 160 which, in turn, flexes the distal end 134 of tube 130 to a desired angle α. Empowering the user to articulate, i.e., flex, the distal end 134 of the tube 130 at various angle α will enable the operator to more effectively target bleeding tissue 50 without causing collateral tissue damage.

Figure 6:
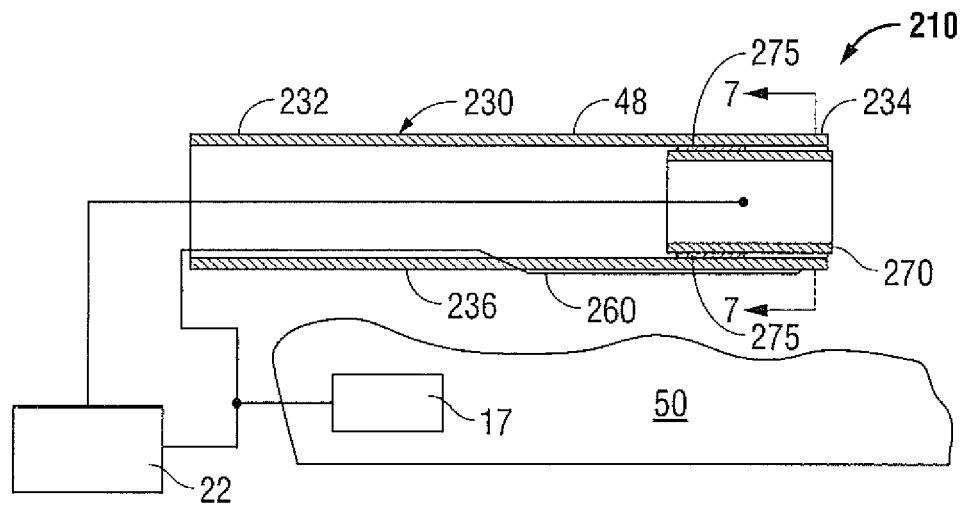
FIG. 6 is an enlarged, side sectional view of another embodiment of the present disclosure showing a ring corona electrode and a dielectric sleeve seated within a flexible catheter and a pull wire/return electrode affixed at the distal end of the flexible catheter.
Figure 7:
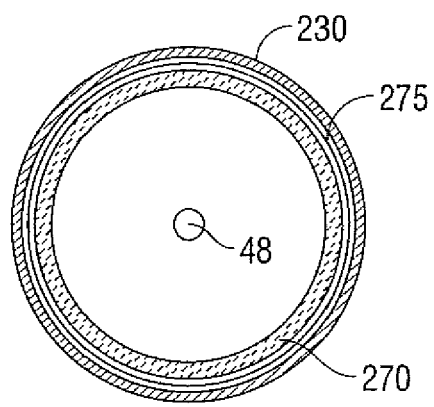
FIG. 7 is a cross sectional view of the FIG. 6 embodiment taken along line 7-7.
Figure 8:
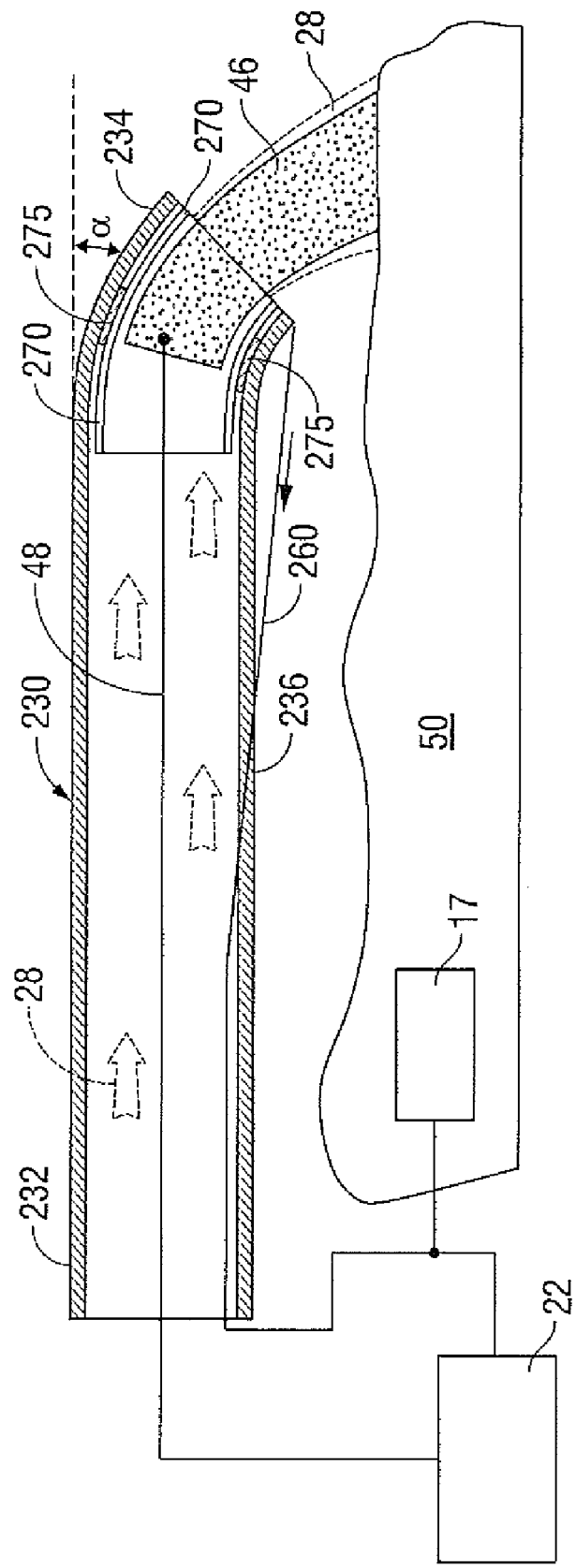
FIG. 8 is an enlarged, side sectional view of the embodiment of FIG. 6 showing the pull wire/return electrode being drawn to articulate the flexible catheter and direct ionized gas at the tissue.

In some cases it may be preferable to utilize wire 160 as a return electrode and couple wire 160 to electrosurgical generator 22. In this case, the portion of wire 160 disposed within tube 130 is preferably insulated to avoid unintentional ignition and ionization of gas 28. FIGS. 6-8 show another embodiment which includes an articulating coagulator 210 having an elongated tube 230 with proximal and distal ends 232 and 234, respectively. Preferably, tube 230 is flexible at or proximate the distal end 234. Coagulator 210 contains many of the same components and features of the FIGS. 4 and 5 embodiment with the exception that a "corona ring" electrode is located at the distal end 234 of tube 230 and is used to initiate ionization of gas 28.

A "corona" is a type of discharge which forms around an active electrode and can be used to increase the reliability of plasma ignition. Coronas are low current discharges and consume very little power and, therefore, do not affect the overall power delivered to the tissue. Coronas typically occur in highly non-uniform electric fields which are commonly generated between electrodes of greatly differing sizes.

A corona electrode is typically located proximate the active electrode 48 and is electrically connected to the return potential of the electrosurgical generator 22. For example and with respect to the FIG. 6 embodiment, a ring corona electrode 275 is disposed at the distal end 234 of tube 230 in coaxial alignment with the active electrode 48.

As seen best in FIG. 7, a dielectric or insulating sleeve 270 is disposed between the corona electrode 275 and active electrode 48 to prevent arcing between electrodes 275 and 48. Preferably, dielectric sleeve 270 is made from a ceramic material or other high temperature resistant material.

When the electrosurgical generator 22 is activated, a non-uniform electric field is generated between corona electrode 275 and active electrode 48 and a corona forms around active electrode 48 which aids in igniting gas 28 to produce gas plasma 46.

As mentioned above, coagulator 210 also includes a wire 260 which is connected at one end proximate the distal end 234 of tube 230 such that retraction of the wire 260 flexes tube 230. Preferably, wire 260 is also connected to corona electrode 275 and performs a dual function: 1) to electrically connect corona electrode 275 to electrosurgical generator 22; and 2) to empower the user with the ability to selectively articulate the distal end 234 of tube 230 at varying angle α to effectively coagulate bleeding tissue 50 in a manner similar to the manner described with respect to the FIG. 4 embodiment.

More particularly and as best seen in FIG. 8, the user can easily direct gas plasma 46 exiting tube 230 transversely at tissue 50 by controlling the tensile force applied to wire 260 which, in turn, articulates distal end 234 to a desired angle α and enables the user to more effectively coagulate or arrest bleeding tissue 50 without causing collateral tissue damage.

From the foregoing and with reference to the various figure drawings, those skilled in the art will appreciate that not only can the coagulator 10, 110 and 210 of the present disclosure be used to arrest bleeding tissue, but the present disclosure can also be employed for desiccating the surface tissue, eradicating cysts, forming eschars on tumors or thermically marking tissue. Those skilled in the art will also appreciate that certain modifications can also be made to the present disclosure without departing from the scope of the present disclosure.

In some cases it may be preferable to use various combinations of the component parts shown with respect to each of the embodiments described herein. For example, it may be preferable to combine a SMA (or a stress-induced martensite) with a wire to articulate the distal end of the tube. In another case it may be preferable to use a ring-like corona return electrode with an SMA to induce plasma ignition.

In some cases it may be preferable to employ an electrode control mechanism to allow a user to selectively adjust the amount of current flowing through the electrodes during surgical conditions. Moreover, even though it may be preferable to use argon as the ionizable gas for promulgating coagulation of the tissue, in some cases it may be preferably to use another ionizable gas to effect the same or different result.

There have been described and illustrated herein several embodiments of a coagulator for arresting bleeding and performing other surgical procedures. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed:

1. A method for coagulating tissue, comprising the steps of:
providing an electrosurgical apparatus including:
an elongated flexible tube defining a longitudinal axis and having a proximal end and a distal end;
a wire connected to the distal end of the tube, wherein the wire acts as a return electrode; and
at least one electrode mounted proximate to the tube for ionizing pressurized ionizable gas;
moving the wire from a first generally relaxed position wherein the tube is disposed in a generally parallel fashion relative to the tissue to a second retracted position wherein the distal end of the tube directs pressurized ionizable gas flowing through the tube at an angle with respect to the longitudinal axis; and
igniting the pressurized ionizable gas through the at least one electrode.

2. A method according to claim 1, further comprising the step of regulating gas flow through the tube.

3. A method according to claim 1, wherein the pressurized ionizable gas is pressurized argon.

4. A method according to claim 1, wherein the angle relative to the longitudinal axis progressively changes proportionally to the amount of tension placed on the wire.

5. A method for coagulating tissue, comprising the steps of:
providing an electrosurgical apparatus including:
an elongated flexible tube having a proximal end and a distal end and defining a longitudinal axis, the tube including a sleeve being selectively extendable therethrough;
a wire connected to the distal end of the tube, wherein the wire acts as a return electrode; and
at least one electrode mounted proximate to the tube for ionizing pressurized ionizable gas;
moving the sleeve from a first position wherein a distal end of the sleeve is disposed in a generally parallel fashion relative to the tissue to a second position wherein the distal end of the sleeve directs pressurized ionizable gas flowing through the sleeve at an angle $\alpha$ with respect to the longitudinal axis; and
igniting the pressurized ionizable gas through the at least one electrode.

6. A method according to claim 5, further comprising the step of regulating gas flow through the tube.

7. A method according to claim 5, wherein the pressurized ionizable gas is pressurized argon.

8. A method according to claim 5, wherein the angle of the distal end of the sleeve relative to the longitudinal axis progressively changes proportionally to the distance the distal end of the sleeve extends from the tube.

* * * * *